(12) United States Patent
Brown

(10) Patent No.: US 9,314,239 B2
(45) Date of Patent: Apr. 19, 2016

(54) METHODS AND DEVICES FOR SECURING SUTURE TO TISSUE

(75) Inventor: Michael C. Brown, Braintree, MA (US)

(73) Assignee: DePuy Mitek, LLC, Raynham, MA (US)

( * ) Notice: Subject to any disclaimer, the term of this patent is extended or adjusted under 35 U.S.C. 154(b) by 792 days.

(21) Appl. No.: 13/478,537

(22) Filed: May 23, 2012

(65) Prior Publication Data

US 2013/0317546 A1 Nov. 28, 2013

(51) Int. Cl.
*A61B 17/04* (2006.01)
*A61F 2/08* (2006.01)

(52) U.S. Cl.
CPC ....... *A61B 17/0401* (2013.01); *A61B 2017/044* (2013.01); *A61F 2002/087* (2013.01); *A61F 2002/0852* (2013.01)

(58) Field of Classification Search
CPC ..................... A61B 17/0401; A61B 2017/044; A61B 2017/0427; A61B 2017/0435; A61F 2002/087; A61F 2002/0852; A61F 2/95; A61F 2/97; A61F 2/2427; A61F 2/2439; A61F 2002/011; A61F 2/82; A61F 2/852; A61F 2/856
USPC .......... 606/151, 213, 215, 232, 233, 300, 153
See application file for complete search history.

(56) References Cited

U.S. PATENT DOCUMENTS

| | | | |
|---|---|---|---|
| 6,214,029 B1 * | 4/2001 | Thill et al. ..................... | 606/213 |
| 6,682,540 B1 * | 1/2004 | Sancoff et al. ................ | 606/153 |
| 7,431,729 B2 * | 10/2008 | Chanduszko ................. | 606/213 |
| 7,695,493 B2 * | 4/2010 | Saadat et al. .................. | 606/215 |
| 8,114,128 B2 | 2/2012 | Cauldwell et al. | |
| 8,133,257 B2 | 3/2012 | Cook et al. | |
| 8,162,974 B2 * | 4/2012 | Eskuri et al. .................. | 606/213 |
| 2002/0042565 A1 | 4/2002 | Cooper et al. | |
| 2003/0093119 A1 | 5/2003 | Zhao et al. | |
| 2006/0224183 A1 * | 10/2006 | Freudenthal .................. | 606/213 |
| 2008/0071310 A1 * | 3/2008 | Hoffman et al. .............. | 606/215 |
| 2009/0076544 A1 | 3/2009 | DiMatteo et al. | |
| 2010/0256775 A1 * | 10/2010 | Belhe .................... | A61F 5/0076 623/23.65 |
| 2011/0118765 A1 * | 5/2011 | Aguirre ......................... | 606/153 |

* cited by examiner

*Primary Examiner* — Jonathan W Miles
*Assistant Examiner* — Lucas Paez

(57) ABSTRACT

Methods and devices are provided for securing suture to tissue. In one exemplary embodiment, the implant can include an intermediate portion, a first radially expandable portion extending from the intermediate portion, and a second radially expandable portion extending from the intermediate portion. The implant can be configured to be inserted through a delivery device in a first configuration and deployed into a hole formed in tissue in a second configuration such that the intermediate portion is positioned within the hole. A suture can be inserted through a passageway of the intermediate portion positioned within the hole, and the suture can be tensioned to secure the tissue to bone.

19 Claims, 6 Drawing Sheets

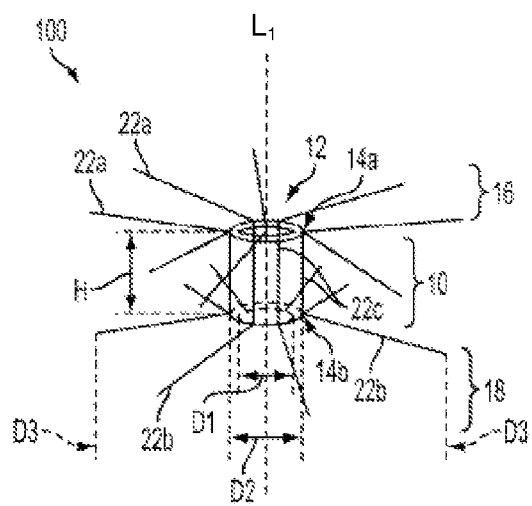
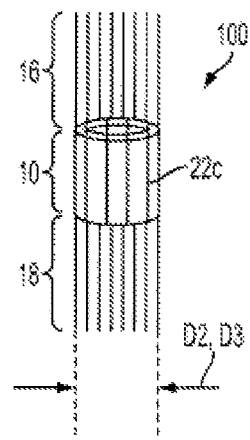
FIG. 1  FIG. 2
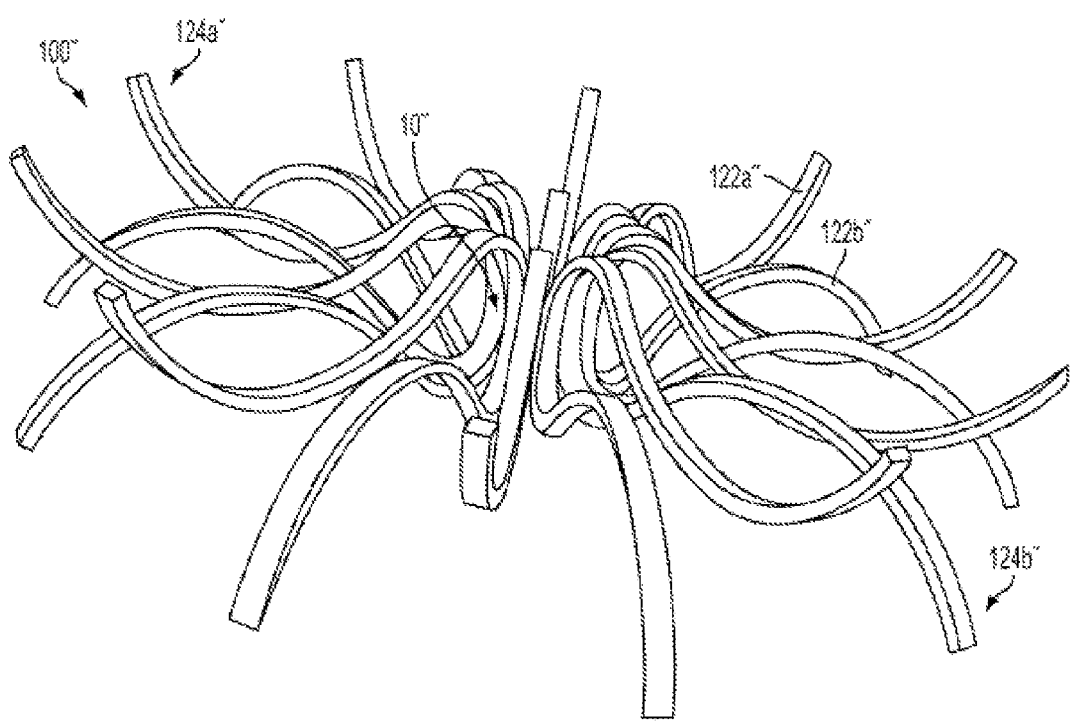
FIG. 3

METHODS AND DEVICES FOR SECURING SUTURE TO TISSUE

FIELD OF THE INVENTION

The present invention relates generally to methods and devices for securing suture to tissue, and in particular to securing suture passed through soft tissue.

BACKGROUND OF THE INVENTION

The complete or partial detachment of ligaments, tendons and/or other soft tissues from their associated bones within the body are commonplace injuries, particularly among athletes. Such injuries generally result from excessive stresses being placed on these tissues. By way of example, tissue detachment may occur as the result of an accident such as a fall, over-exertion during a work-related activity, or during the course of an athletic event. In the case of a partial detachment, the injury will frequently heal itself, if given sufficient time and if care is taken not to expose the injury to further undue stress. In the case of complete detachment, however, surgery is often needed to re-attach the soft tissue to its associated bone.

Numerous devices are currently available to re-attach soft tissue to bone. Examples of such devices include screws, staples, suture anchors and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is drilled into the bone, through a drill guide, at the desired point of tissue re-attachment. Next, a suture anchor is deployed through the drill guide and into the hole using an appropriate installation tool. This effectively locks the suture to the bone, with the free ends of the suture and a suture extending out of the bone. The suture can extend through or around the soft tissue, and the suture can be tensioned by pulling the suture to secure the soft tissue to the bone. However, pulling the suture can cause damage to the tissue, such as by causing the suture to partially or fully break through the damaged tissue, which is often referred to as "cheese wiring" through the tissue. The likelihood of causing such damage increases based on factors such as the tissue being compromised prior to the re-attachment procedure, the tissue having a low density, and/or the direction of the pulling force relative to tissue fibers. This tissue damage can greatly disrupt the healing process, and surgical intervention may be needed to reattach the tissue to the bone.

Accordingly, there remains a need for improved methods and devices for securing suture to tissue.

SUMMARY OF THE INVENTION

In one embodiment, a surgical method is provided that includes advancing an implant through a cannula in a first configuration, the implant having an intermediate portion with a first radially expanding portion extending distally therefrom and a second radially expanding portion extend proximally therefrom. The implant can be advanced distally out of the cannula to position the implant within an opening formed in soft tissue. More specifically, the implant can move from the first configuration to a second radially expanded configuration such that the first radially expanding portion of the implant is positioned on a distal side of the opening, the second radially expanding portion of the implant are positioned on a proximal side of the opening, and the intermediate portion is positioned within the opening formed in the tissue. A suture can be advanced through the intermediate portion of the implant that is positioned in the soft tissue.

The implant can vary in any number of ways. The implant can be formed from a shape memory material such that the implant is biased to the second configuration. A maximum outer diameter of the implant in the first configuration can be less than a maximum inner diameter of an inner passageway of the cannula in which the implant is disposed, and a maximum outer diameter of the implant in the second configuration can be greater than the maximum inner diameter of the inner passageway.

The surgical method can include a variety of modifications. For example, advancing the implant distally out of the cannula can include advancing the first radially expandable portion out of the cannula before the second radially expandable portion is advanced out of the cannula. For another example, prior to advancing the implant out of the cannula, the opening can be formed in the soft tissue. For yet another example, after advancing the suture, the suture can be tensioned relative to bone.

In one embodiment, the first radially expandable portion can include a first plurality of legs extending distally from the intermediate portion, and the second radially expandable portion can include a second plurality of legs extending proximally from the intermediate portion. When the implant is in the first configuration, the first plurality of legs and the second plurality of legs can each be substantially straight, and when the implant is in the second configuration, the first plurality of legs and the second plurality of legs can each be bent. When the implant is in the first configuration, longitudinal axes of each of the first plurality of legs can be substantially parallel to longitudinal axes of each of the second plurality of legs and to a longitudinal axis of the cannula, and when the implant is in the second configuration, the longitudinal axes of the first plurality of legs and the longitudinal axes of each of the second plurality of legs can extend transverse to the longitudinal axis of the cannula. Advancing the implant distally out of the cannula can include advancing the first plurality of legs out of the cannula before the second plurality of legs are advanced out of the cannula. When the first plurality of legs are advanced out of the cannula before the second plurality of legs are advanced out of the cannula, the implant can be in a third configuration in which the longitudinal axes of the first plurality of legs extend transverse to the longitudinal axis of the cannula and the longitudinal axes of the second plurality of legs are substantially parallel to the longitudinal axis of the cannula.

In another embodiment, the first radially expandable portion can include a first fabric extending distally from the intermediate portion, and the second radially expandable portion can include a second fabric extending proximally from the intermediate portion. Additionally, the first fabric and the second fabric can be formed from one continuous piece of fabric.

In another embodiment, a surgical method is provided that includes advancing an introducer device at least partially through an opening formed in tissue. The introducer device can have an implant disposed in an inner passageway thereof. Moving a first radially expanding portion of the implant out of the inner passageway can cause the first radially expanding portion to be positioned on a distal side of the opening, the first radially expanding portion expanding into contact with a distal surface of the tissue. Moving a second radially expanding portion of the implant out of the inner passageway can position the second radially expanding portion on a proximal side of the opening. The second radially expanding portion can expand into contact with a proximal surface of the tissue. A hollow intermediate portion of the implant extending between the first radially expanding portion and the second radially expanding portion can be positioned within the opening, and a suture can be advanced through the hollow intermediate portion positioned within the opening.

The opening in the tissue can be formed by performing at least one of advancing the introducer device through the tissue and cutting through the tissue. Moving the first radially expanding portion can include moving the implant distally relative to the introducer device, and moving the second radially expanding portion can include moving the introducer device proximally relative to the implant. Moving the first radially expanding portion of the implant out of the inner passageway can cause the first radially expanding portion to automatically expand radially away from a central longitudinal axis of the implant, and moving the second radially expanding portion legs of the implant out of the inner passageway can cause the second radially expanding portion to automatically expand radially away from the central longitudinal axis of the implant.

The implant can have a variety of configurations. In one embodiment, the first radially expandable portion can include a first plurality of legs extending distally from the hollow intermediate portion, and the second radially expandable portion can include a second plurality of legs extending proximally from the hollow intermediate portion.

BRIEF DESCRIPTION OF THE DRAWINGS

The invention will be more fully understood from the following detailed description taken in conjunction with the accompanying drawings, in which:

FIG. 1 is a perspective view of one embodiment of an implant in an expanded configuration and including a plurality of legs;

FIG. 2 is perspective view of the implant of FIG. 1 in a compressed configuration;

FIG. 3 is a perspective view of another embodiment of an implant in an expanded configuration and including a plurality of legs;

DETAILED DESCRIPTION OF THE INVENTION

Figure 4:
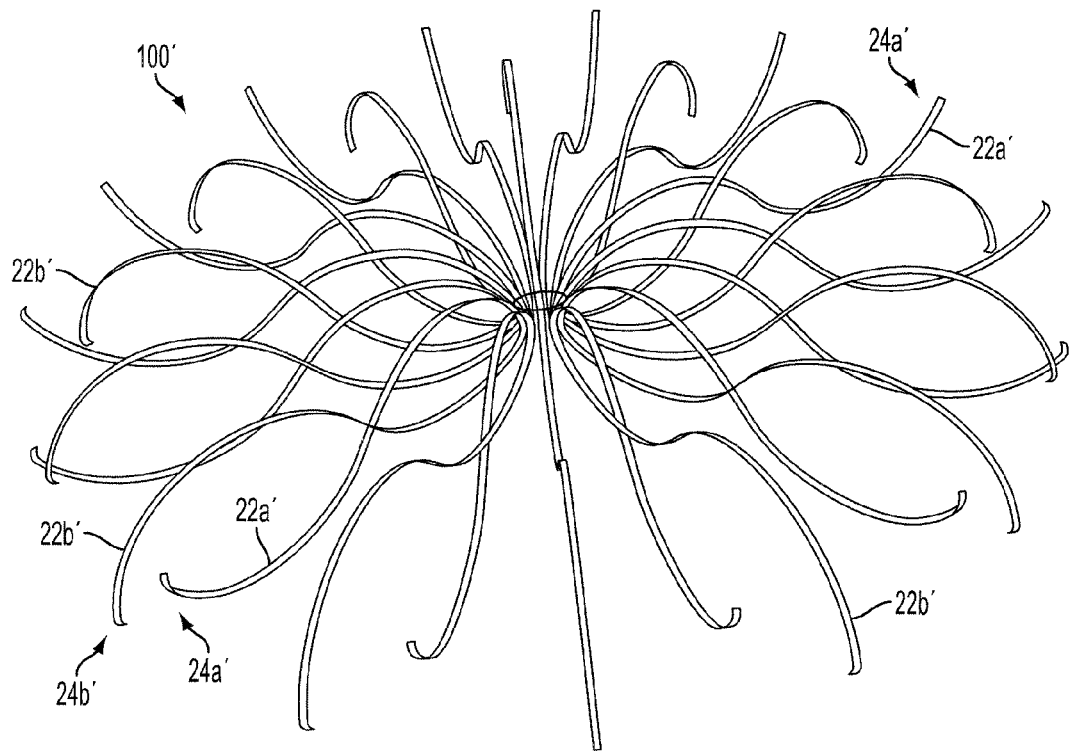
FIG. 4 is a perspective view of yet another embodiment of an implant in an expanded configuration and including a plurality of legs.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various methods and devices are provided for securing tissue to bone. In general, the methods and devices can facilitate securing suture to tissue. In one exemplary embodiment, an implant, grommet, or eyelet, generally referred to herein an as "implant," is provided and is configured to be positioned in tissue. The implant can include an intermediate portion, a first expandable portion extending from the intermediate portion, and a second expandable portion extending from the intermediate portion. The implant can be deployed into a hole formed in tissue, such that the intermediate portion is positioned within the hole, and to expand into a second configuration to thereby engage the tissue. A suture can be inserted through a passageway formed in the intermediate portion of the implant, and the suture can be tensioned to secure the tissue to bone. By positioning the implant in the hole formed in the tissue and passing the suture through the implant, direct contact of the suture with tissue within the hole can be reduced, if not entirely prevented. This can help prevent the suture from cheese wiring or breaking through the tissue, thereby facilitating healing and reducing chances of damaging the tissue. The implant can therefore facilitate tensioning of the suture in which a force is applied to the suture to draw the tissue into optimal contact with the bone because the implant can allow a greater force to be applied to the suture without the suture breaking through the tissue. This can also allow the tissue to be positioned in better contact with the bone, which can facilitate healing. Additionally, since the implant can reduce chances of the tissue being damaged and needing replacement during the procedure, which can involve preparation and introduction of another replacement tissue into the body, the implant can help save time and resources. The implant can also reduce chances of the suture breaking through the tissue after the surgical procedure and during the healing process when the tissue and/or the suture can shift within the body, which can facilitate healing and reduce chances of follow-up surgery being required to repair or replace damaged tissue.

The implants disclosed herein can be formed from any one or more materials, preferably a biocompatible material(s)

safe for use in the body. In an exemplary embodiment, the implant can be formed at least partially from a shape memory material, which can include a single material or a combination of materials. However, the implant can be made from any type of material and any combination of materials able to provide structure to the implant as discussed below and as appropriate for use in a body. Non-limiting examples of shape memory materials include copper-zinc-aluminum-nickel alloys, copper-aluminum-nickel alloys, nickel-titanium alloys such as Nitinol, thermoplastic materials such as Nylon or Nylon blends, and shape memory polymers such as Veriflex™. The shape memory material can facilitate the implant being naturally biased to an expanded configuration in which it can be positioned in tissue, as discussed further below. The shape memory material can also facilitate delivery of the implant into tissue by allowing any or all portions of the implant to be deformed or bent into a compressed configuration in which the implant has a relatively small diameter to facilitate delivery of the implant to tissue while also allowing the implant to automatically move from the compressed configuration to the implant's "memorized" shape, in which it has a larger diameter, for implantation within the tissue. In an exemplary embodiment, the entire implant can be formed from one or more shape memory materials. In another exemplary embodiment, radially expandable portions of the implant can be formed from one or more shape memory materials, and another portion of the implant, e.g., an intermediate portion from which the radially expandable portions extend, can be formed of a non-shape memory material, e.g., titanium.

The implants disclosed herein can optionally have a drug coating, similar to a drug-eluting stent, that can break down over time to release a drug to, e.g., help reduce chances of infection, cell proliferation (e.g., hyperplasia), and/or other possible adverse effects from the presence of the implant in the body. Any drug coating can be used, as will be appreciated by a person skilled in the art. The implant can have any coloration, such as a dark color, e.g., dark blue, dark gray, black, etc., which can help enhance the implant's visibility when disposed in a body.

Generally, an implant can be configured to be positioned within tissue. In one embodiment, the implant can be configured to move between a compressed configuration, in which the implant has a first maximum diameter, and an expanded configuration, in which the implant has a second maximum diameter that is greater than the first diameter. In this way, as discussed further below, the implant can be delivered into a patient's body in the compressed configuration through a relatively small opening, e.g., through a relatively small skin incision, and move to the expanded configuration within the patient's body so as to be implanted therein in the larger expanded configuration. Non-limiting examples of tissue into and through which the implants disclosed herein can be positioned include connective tissue such as rotator cuff tissue in the shoulder, where the tissue thickness is typically in a range of about three to six millimeters, and in the hip, where the connective tissue is typically in a range of about five to fifteen millimeters thick.

FIGS. 1 and 2 illustrate one exemplary embodiment of an implant 100 configured to be positioned within tissue and to be movable between different configurations in which the implant 100 has different maximum diameters. The implant 100 can include an intermediate portion 10 having a first radially expanding portion 16 and a second radially expanding portion 18 extending therefrom. The first radially expanding portion 16 can include a first plurality of legs 22a, and the second radially expanding portion can include a second plurality of legs 22b. Generally, the first and second plurality of legs 22a, 22b can be configured to compress toward and radially expand away from the intermediate portion 10, e.g., toward and away from a central longitudinal axis $L_1$ of the implant 100, to move the implant 100 between expanded and compressed configurations.

FIG. 1 shows the implant 100 in the expanded configuration, and FIG. 2 shows the implant 100 in the compressed configuration. The implant 100 can be biased to the expanded configuration, such as by being at least partially formed of a shape memory material "memorized" to the expanded configuration. The implant 100 can therefore be configured to naturally be in the expanded configuration and to be in the compressed configuration when an external force is applied thereto, such as by the implant 100 being compressed by hand and/or being positioned within a cannula, as discussed further below. For clarity of illustration, FIG. 2 omits the external force. Because the implant 100 can be formed from a shape memory material, the legs 22a, 22b can be configured to automatically move between the expanded and compressed configurations, e.g., depending on whether the external force is being applied to the implant 100 or not.

The intermediate portion 10 can have a variety of sizes, shapes, and configurations. For non-limiting example, the intermediate portion 10 can have a ring-shape such as a substantially cylindrical shape and a substantially circular cross-sectional shape, as shown in FIGS. 1 and 2. In other embodiments, the intermediate portion can have another shape, e.g., an hourglass shape, a cone shape, a rectangular cross-sectional shape, etc.

The intermediate portion 10 can be hollow such that it has open ends with a passageway, lumen, or channel 12, generally referred to herein as a "channel," extending therethrough. The channel 12 can extend along the central longitudinal axis $L_1$ of the implant 100, e.g., a central longitudinal axis of the intermediate portion 10, between proximal and distal ends 14a, 14b of the intermediate portion 10. The channel 12 can be configured to receive at least one suture (not shown) therein, as discussed further below. One or both of the proximal end 14a and the distal end 14b of the intermediate portion 10 can have rounded or smoothed edges, which can help prevent a suture extending through the channel 12 from snagging or fraying against the proximal and distal ends 14a, 14b of the implant 100 through which the suture passes. The channel 12 in the illustrated embodiment has a constant maximum inner diameter D1 and a constant maximum outer diameter D2, subject to manufacturing tolerances as will be appreciated by a person skilled in the art. However, the intermediate portion's maximum inner diameter and/or maximum outer diameter can vary, e.g., when the intermediate portion has an hourglass outer shape, a conical outer shape, a conical channel, a spherical outer shape, etc. The intermediate portion 10 can have a relatively thin wall such that a difference between the maximum inner diameter D1 maximum outer diameter D2 is relatively small. A relatively thin wall can provide for relatively large openings at the intermediate portion's open ends, which can ease passage of the suture into the channel 12.

The maximum outer diameter D2 of the intermediate portion 10 can define a maximum diameter of the implant 10 in the compressed configuration. In other words, the first and second radially expanding portions 16, 18 can each be configured to compress to a diameter equal to or less than the maximum outer diameter D2 of the intermediate portion 10. As in this illustrated embodiment, the intermediate portion 10 can be formed from a relatively rigid material such as titanium, e.g., not be formed from compressible material such as a shape memory material, such that the maximum outer diameter D2 of the intermediate portion 10 can remain the same whether the implant 100 is in the expanded configuration or the compressed configuration. In other words, the intermediate portion can be non-deformable and non-compressible.

An interior surface of the intermediate portion 10, e.g., the surface defining the channel 12, can be substantially smooth, as in this illustrated embodiment, which can facilitate free slidable movement of a suture therethrough. In some embodiments, the intermediate portion's interior surface can include at least one suture retaining feature configured to freely allow the suture to slide therethrough, e.g., during initial passage of the suture therethrough the channel 12 and during tensioning of the suture, while also being configured to reduce movement or migration of the suture within the channel 12 after the suture is tensioned and secured within a patient's body. The at least one suture retaining feature can therefore help prevent a suture seated therein from potentially snagging or fraying the suture against the implant by moving within the channel after the suture is tensioned and secured within a patient. Non-limiting examples of suture retaining features include a textured surface, a sticky surface, a longitudinal groove formed in the intermediate portion's internal surface, and a leg extending at least partially along the interior surface of the intermediate portion.

An exterior surface of the intermediate portion 10 can be substantially smooth, as in this illustrated embodiment, which can facilitate positioning of the intermediate portion 10 within a tissue hole. In some embodiments, the intermediate portion's exterior surface can include at least one tissue gripping feature configured to increasing a frictional force between an implant and a tissue hole in which the implant is seated to help secure the implant within the hole and reduce movement or migration of the implant therein after the intermediate portion is positioned within a tissue hole. The at least one tissue gripping feature can therefore cooperate with the implant's radially expanding portions to help prevent the implant from moving or migrating within the tissue hole. Non-limiting examples of tissue gripping features include a textured surface, a sticky surface, and a leg extending at least partially along the exterior surface of the intermediate portion.

As in the illustrated embodiment, a longitudinal length or height H of the intermediate portion 10, generally referred to as "height," can be less than a depth of a hole formed in the tissue into which the implant 100 can be positioned, which can help prevent the implant 100 from extending too far beyond surfaces of the tissue when deployed in the hole and potentially impinging on adjacent tissue and/or other structures. The radially expandable portions 16, 18 of the implant 100 can compensate for the discrepancy between the height H and the hole depth by radially expanding out of the hole to securely hold the implant 100 therein. Alternatively, the height H of the intermediate portion can be equal to or greater than the depth of the hole formed in the tissue, which can provide a larger contact area between an exterior surface of the implant and the hole for stability and reinforcement of the tissue. In an exemplary embodiment, the height H of the intermediate portion 10 can be in a range of about two to eight millimeters, which can facilitate use of the implants in shoulder rotator cuff repairs.

The first and second radially expanding portions 16, 18, e.g., the legs 22a, 22b, in this illustrated embodiment can be formed from at least one shape memory material. The first and second radially expanding portions 16, 18 can therefore each be configured to be compressible to a diameter equal to or less than the maximum outer diameter D2 of the intermediate portion 10. The first and second radially expanding portions 16, 18 can be configured to radially expand relative to the intermediate portion 10 from a compressed configuration in which the diameter is equal to or less than the maximum outer diameter D2 of the intermediate portion 10, and an expanded configuration in which a maximum diameter D3 is greater than the maximum outer diameter D2 of the intermediate portion 10. The maximum diameter D3 of the first and second radially expanding portions 16, 18 can therefore define a maximum diameter of the implant 10 in the expanded configuration. Although the first and second radially expanding portions 16, 18 in the illustrated embodiment both have the same maximum diameter D3, subject to manufacturing tolerances as will be appreciated by a person skilled in the art, one of an implant's radially expanding portions can have a maximum diameter that is greater than a maximum diameter of the other radially expanding portion. Having different maximum diameters in the radially expanding portions can facilitate use of the implant with irregularly shaped tissue in which one side of the tissue has a greater surface area than the other side.

The first and second plurality of legs 22a, 22b of the implant 100 can have a variety of sizes, shapes, and configurations. The first plurality of legs 22a can extend proximally from the proximal end 14a of the intermediate portion 10, and the second plurality of legs 22b can extend distally from the distal end 14b of the intermediate portion 10. The legs 22a, 22b can all have the same length and width, or any of the legs 22a, 22b can have lengths and/or widths that differ from any of the other legs. In the illustrated embodiment, the implant 100 includes eight first legs 22a and eight second legs 22b, but an implant can include any number of first and second legs, same or different from one another. In an exemplary embodiment, an implant can include at least two first legs and at least two second legs, which can facilitate securing the implant within a tissue hole, as discussed further below.

The lengths of the first and second plurality of legs 22a, 22b of the implant 100 can also vary relative to the height of the intermediate portion 10. For example, the legs 22a, 22b can each have a length that is greater than, substantially equal to, or less than the height of the intermediate portion. In an exemplary embodiment, at least one of the plurality of legs 22a, 22b can have a length that is greater than or substantially equal to the height of the intermediate portion. In the illustrated embodiment, the legs 22a, 22b of the implant 100 each have a length greater than the height of the intermediate portion. This can provide additional gripping forces between the legs 22a, 22b and the surface of the tissue to better secure the implant within the hole formed in tissue.

The first and second plurality of legs 22a, 22b can be spaced around the proximal and distal ends 14a, 14b, respectively, of the intermediate portion 10 in a variety of orientations. In an exemplary embodiment, the first plurality of legs 22a can be spaced equidistantly around a perimeter of the proximal end 14 of the intermediate portion 10, and the second plurality of legs 22b can be spaced equidistantly around a perimeter of the distal end 14 of the intermediate portion 10. Such equidistant spacing can facilitate the legs 22a, 22b securely gripping tissue in which the intermediate portion 10 is positioned all around, e.g., 360° around, the proximal and distal perimeters. The legs can have other spacing in other embodiments.

The first and second plurality of legs 22a, 22b can be configured to extend at different angles relative to the intermediate portion 10 depending on whether the implant 100 is in the expanded configuration or the compressed configuration. When the implant 100 is in the expanded configuration, as shown in FIG. 1, each of the legs 22a, 22b can be configured to have a linear or straight configuration such that at least the region adjacent to the intermediate portion extends substantially perpendicular to the longitudinal axis $L_1$ of the implant 100, e.g., extend at an angle of about 90° relative to the longitudinal axis $L_1$ of the implant 100. Depending on the tissue in which the implant 100 is deployed, e.g., depending on tissue thickness, tissue surface variations, tissue pliability, etc., one or more of the legs 22a, 22b may not expand to be oriented substantially perpendicularly relative to the intermediate portion 10. Extending substantially perpendicularly can help maximize a surface area of each of the legs 22a, 22b that can contact a tissue surface when expanded thereagainst, thereby helping to retain the implant 100 within the tissue, as discussed further below. When the implant 100 is in the compressed configuration, as shown in FIG. 2, each of the legs 22a, 22b can be configured to be oriented substantially parallel to each other and to the longitudinal axis $L_1$ of the implant 100, e.g., extend at an angle of about 0° relative to the longitudinal axis $L_1$ of the implant 100. Depending on the force being applied to the implant 100 to hold the implant 100 in the compressed configuration, e.g., depending on a diameter of a cannula in which the implant 100 is positioned, depending on how hard fingers press the legs 22a, 22b inward, etc., one or more of the legs 22a, 22b may not be oriented substantially parallel to the longitudinal axis $L_1$ of the implant 100.

The legs 22' can be positioned in a variety of different ways. In particular, the first set of legs 16' of the implant 100' can be angularly offset from the second set of legs 18', as shown in FIGS. 2 and 3.

The first and second plurality of legs 22a, 22b can be mated to the intermediate portion 10 in a variety of ways. In this illustrated embodiment, each of the first and second plurality of legs 22a, 22b is part of a continuous leg strand that includes one of the first legs 22a, one of the second legs 22b, and a connector leg 22c extending between the ones of the first and second legs 22a, 22c. In other words, the implant 100 can be configured to include a first number of continuous leg strands, e.g., eight, with each of the continuous leg strands including one connector leg 22c, one first leg 22a, and one second leg 22b such that the implant 100 includes an equal number of first, second, and connector legs 22a, 22b, 22c, e.g., eight. The connector leg 22c can be configured to mate the continuous strands, and thereby mate the first and second legs 22a, 22b, to the intermediate portion 10. The connector legs 22c can extend along the intermediate portion 10 to so mate the continuous strands thereto, such as by extending longitudinally along the exterior surface of the intermediate portion 10, as shown in FIGS. 1 and 2. The first and second plurality of legs 22a, 22b can therefore be positioned symmetrically with one another. Although the connector legs 22c extend longitudinally along the intermediate portion 10 substantially parallel to the longitudinal axis $L_1$ of the implant 100, the connector legs 22 can extend transversely to the longitudinal axis $L_1$ of the implant 100. Extending along the exterior surface of the intermediate portion 10 can allow the connector legs 22c to act as tissue gripping features. In another embodiment, connector legs can extend longitudinally or otherwise along an interior surface of an intermediate portion, thereby allowing the connector legs to act as suture retaining features. In yet another embodiment, connector legs can extend longitudinally or otherwise along an intermediate portion and be sandwiched between two or more layers of material forming the intermediate portion. In an exemplary embodiment, all legs mated to an intermediate portion are mated thereto in the same way, e.g., all along an exterior surface thereof, but any of the legs can be mated to the intermediate portion differently than any of the other legs.

Alternatively, an implant can include discrete proximal and distal legs such that a first plurality of the legs mated to an intermediate portion are discrete from a second plurality of legs mated to the intermediate portion. In other words, the implant can lack connector legs. For non-limiting example, instead of an implant including eight total discrete leg strands resulting in sixteen leg extensions as in the implant 100 of FIGS. 1 and 2, an implant can include sixteen total discrete leg strands resulting in sixteen leg extensions.

The legs 22a, 22b can be discrete elements fixedly mated to the intermediate portion 10 via the connector legs 22c. Alternatively, legs can be integrally formed with an intermediate portion. In one embodiment, the legs can be molded with the intermediate portion as a single unit. In another embodiment, the legs can form the intermediate portion, e.g., connector legs forming the intermediate portion. The legs can therefore define interior and exterior surfaces of the intermediate portion.

FIG. 3 illustrates an exemplary embodiment of an implant 100" including a first plurality of legs 122a", a second plurality of legs 122b", and an intermediate portion 10" formed from the first and second legs 122a", 122b". The implant 100" of FIG. 3 and its various elements can be generally configured and used similar to other like-named elements discussed herein. Each of the first plurality of legs 122a" can have a first terminal portion mated to a corresponding first terminal portion of one of the second plurality of legs 122b", e.g., longitudinal sides of the first terminal portions mated together such as by welding or adhesive. The first terminal portions of the legs 122a", 122b" can therefore form the intermediate portion 10" of the implant 100". Second terminal portions of the first plurality of legs 122a" can extend proximally from the intermediate portion 10" and define a first radially expandable portion of the implant 100". Second terminal portions of the second plurality of legs 122b" can extend distally from the intermediate portion 10" and define a second radially expandable portion of the implant 100". The first and second plurality of legs 122a", 122b" can therefore be positioned asymmetrically or angularly offset from one another. The implant 100" of FIG. 3 illustrates an embodiment of an implant formed entirely from a shape memory material.

Similar to the implant 100 of FIGS. 1 and 2, the first and second legs 122a", 122b" can be configured to be oriented substantially parallel to each other and to a longitudinal axis of the implant 100" when the implant 100" is in the compressed configuration. In contrast to the implant 100 of FIGS. 1 and 2, when the implant 100" is in the expanded configuration, each of the first and second legs 122a", 122b" can be configured to have a curved configuration in which the second terminal portions of each of the first and second legs 122a", 122b" are non-linear or non-straight. The curvature of the first and second legs 122a", 122b" can vary, but as in this illustrated embodiment, the first and second legs 122a", 122b" can have a curved "S" shape. Terminal ends 124a", 124b" of the legs 122a", 122b" can therefore be configured to curve in a direction away from the intermediate portion 10" when the implant 100" is in the expanded configuration. In other words, the terminal ends 124a" of the first plurality of legs 122a" can be configured to curve in a proximal direction, and the terminal ends 124b" of the second plurality of legs 122b" can be configured to curve in a distal direction. The curved configuration of the legs 122a", 122b" and the curved terminal ends of the legs 122a", 122b" can help prevent the legs 122a", 122b'' from tearing, puncturing, or otherwise damaging tissue when the implant 100'' is deployed within the tissue in the expanded configuration.

FIG. 4 illustrates another exemplary embodiment of an implant 100' having first and second plurality of legs 22a', 22b' configured to have a curved configuration and curved terminal ends 24a', 24b' when the implant 100' is in an expanded configuration. The terminal ends 24a', 24b' can have enlarged diameters, e.g., be configured as balls or blocks, compared to remainder of their respective legs 22a', 22b'. The enlarged diameters can help prevent the terminal ends 24a', 24b' from tearing, puncturing, or otherwise damaging tissue or other matter near the implant 100'. The first and second plurality of legs 22a', 22b' can extend from opposed proximal and distal ends of an intermediate portion 10' of the implant, which in this illustrated embodiment has a ring or cylindrical shape. The implant 100' of FIG. 4 also illustrates an embodiment of an implant formed entirely from a shape memory material. The implant 100' of FIG. 4 and its various elements can be generally configured and used similar to other like-named elements discussed herein.

FIGS. 1-4 illustrate embodiments of implants having radially expanding portions each including a plurality of legs configured to radially extend outward from and inward toward a central longitudinal axis of the implant. However, an implant's radially expanding portions can have different configurations. For non-limiting example, an implant can have radially expanding portions including fabric configured to radially extend outward from and inward toward a central longitudinal axis of the implant. A radially expanding portion including fabric can allow the implant to directly contact tissue over a greater surface area of the tissue than a radially expanding portion including a plurality of legs, which can help secure the implant within a hole formed in the tissue and/or help prevent slippage of the implant relative to the tissue while the implant is implanted within the hole. For another non-limiting example, an implant can include a radially expanding portion including fabric and a radially expanding portion including a plurality of legs.

Figure 5:
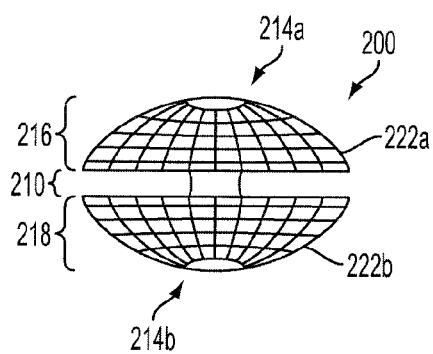
FIG. 5 is a perspective view of one embodiment of an implant in an expanded configuration and including a fabric.
Figure 6:
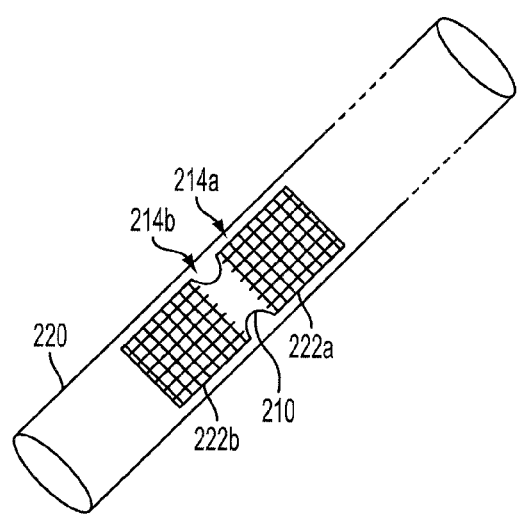
FIG. 6 is perspective, partially transparent view of the implant of FIG. 5 in a compressed configuration and disposed in a delivery device.

FIGS. 5 and 6 illustrate an exemplary embodiment of an implant 200 including radially expanding portions 216, 218 each including fabric. In one embodiment, the fabric can be separate and discrete for each of the radially expanding portions 216, 218 such that the implant 200 includes at least two fabrics, e.g., one fabric for the first radially expanding portion 216 and another fabric for the second radially expanding portion 218. In another embodiment, the fabric can be continuous between the radially expanding portions 216, 218 and the intermediate portion 210 such that the implant 200 is formed from one continuous piece of fabric. The implant 200 of FIGS. 5 and 6 and its various elements can be generally configured and used similar to other like-named elements discussed herein. FIG. 5 illustrates the implant 200 in an expanded configuration, and FIG. 6 illustrates the implant 200 in a compressed configuration. A force holding the implant 200 in the compressed configuration is provided by an elongate tubular member 220, e.g., a cannula, a trocar, a delivery tube, an endoscopic channel, etc., in which the implant 200 is disposed.

The implant 200 can be configured to be positioned within tissue and to be movable between different configurations, e.g., expanded and compressed configurations, in which the implant 200 has different maximum diameters. The implant 200 can include an intermediate portion 210 having the first radially expanding portion 216 extending proximally therefrom and having the second radially expanding portion 218 extending distally therefrom. The first radially expanding portion 216 can extend from a proximal end 214a of the intermediate portion 210, and the second radially expanding portion 218 can extend from a distal end 214b of the intermediate portion 210. The intermediate portion 210 in this illustrated embodiment includes a cannulated hourglass-shaped member having the first and second radially expanding portions 216, 218 mated to the open ends of the hourglass. The first radially expanding portion 216 can extend continuously from the proximal end 214a, e.g., from around an entire perimeter or circumference of the proximal end 214a, and the second radially expanding portion 218 can extend continuously from the distal end 214b, e.g., from around an entire perimeter or circumference of the distal end 214b.

In this embodiment, the first radially expanding portion 216 includes a first fabric 222a, and the second radially expanding portion 218 includes a second fabric 222b. The first and second fabrics 222a, 222b each have a same size, shape, and configuration in this embodiment, but an implant can have differing first and second fabrics. The first and second fabrics 222a, 222b can be formed from a variety of materials. The first and second fabrics 222a, 222b can each be made from any type of flexible material, same or different from one another, appropriate for use in a body, such as mesh (braided or unbraided), fiber (natural or synthetic), gauze-like cloth, and other similar types of material. In an exemplary embodiment, the fabrics 222a, 222b each include braided mesh, as tissue is generally less likely to stick or snag on braided mesh than on other materials. The fabrics 222a, 222b can be formed entirely from one or more shape memory materials, as in the illustrated embodiment in which the fabrics 222a, 222b each include a web-like mesh formed entirely from a shape memory material. An implant can, however, include one or more radially expanding portions partially formed of a shape memory material.

Figure 7:
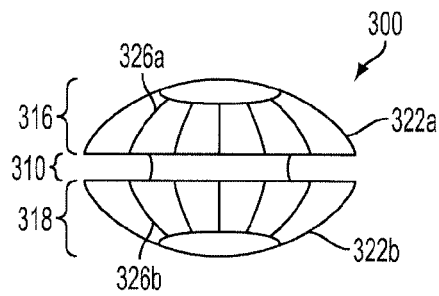
FIG. 7 is a perspective view of another embodiment of an implant in an expanded configuration and including a fabric.

FIG. 7 illustrates another exemplary embodiment of an implant 300 including radially-expandable fabric. The implant 300 can be configured to be positioned within tissue and to be movable between different configurations in which the implant 300 has different maximum diameters. The implant 300 of FIG. 7 and its various elements can be generally configured and used similar to other like-named elements discussed herein. The implant 300 can include an intermediate portion 310 having a first radially expanding portion 316 and a second radially expanding portion 318 each extending therefrom.

The first radially expanding portion 316 includes a first fabric 322a, and the second radially expanding portion 318 includes a second fabric 322b. The first and second fabrics 322a, 322b in this illustrated embodiment each include a flexible material, e.g., mesh, fiber, gauze-like cloth, and other similar types of material, mated to pieces of shape memory material. The pieces of shape memory material can have a variety of sizes and shapes, e.g., rings, rods, wires, braids, etc. In this illustrated embodiment, the shape memory material includes a plurality of wires 326a, 326b inlaid in each of the radially expanding portion's fabric material in a radial arrangement similar to spokes of an umbrella. Although the shape memory material is inlaid in the fabric material, the shape memory material can be mated to fabric material in other ways, such as weaving, gluing, etc.

Figure 8:
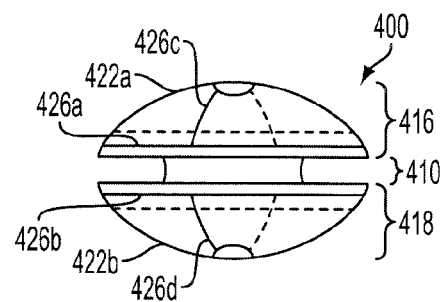
FIG. 8 is a perspective view of yet another embodiment of an implant in an expanded configuration and including a fabric.

FIG. 8 illustrates yet another exemplary embodiment of an implant 400 including radially-expandable fabric. The implant 400 can be configured to be positioned within tissue and to be movable between different configurations in which the implant 400 has different maximum diameters. The implant 400 of FIG. 8 and its various elements can be generally configured and used similar to other like-named elements discussed herein. The implant 400 can include an intermediate portion 410 having a first radially expanding portion 416 and a second radially expanding portion 418 each extending therefrom. The first radially expanding portion 416 includes a first fabric 422a, and the second radially expanding portion 418 includes a second fabric 422b. The first and second fabrics 422a, 422b in this illustrated embodiment each include a flexible material mated to a piece of shape memory material in the form of a circumferential ring 426a, 426b and a radial support 426c, 426d. In this illustrated embodiment, the rings 426a, 426b can each be located adjacent terminal ends of their respective fabrics, e.g., terminal ends opposite terminal ends mated to the intermediate portion 410, which can facilitate contact of the fabric material with tissue when the intermediate portion 410 is positioned within a hole formed in tissue. The supports 426c, 426d can each help move their respective rings 426a, 426b into contact with a tissue surface when the implant 400 is deployed in tissue, e.g., by directing their respective rings 426a, 426b toward the intermediate portion 410.

Various delivery devices can be used to deliver an implant into tissue. In general, a delivery device configured to deliver any of the implants discussed herein into a body of a patient can have a passageway extending therethrough that can be sized to allow an implant to be advanced therethrough. The delivery device can be configured to deploy an implant in tissue inside or outside a patient's body. Generally, for deployment inside a patient's body, the delivery device can be configured to be inserted through an opening in a patient's body, e.g., an incision formed in a patient, to position a proximal end of the delivery device outside the patient and a distal end of the delivery device within the patient. With the distal end of the delivery device positioned within the patient, the distal end of the delivery device can be positioned adjacent a tissue, and an implant can be advanced through the passageway of the delivery device and into the tissue. The delivery device can be configured to have the implant positioned with the passageway thereof when the delivery device is inserted into the patient, although in some embodiments, the implant can be positioned within the passageway of a delivery device after the delivery device is inserted into a patient. Deployment outside a patient's body can generally be the same as deployment inside a patient's body, except that the tissue in which the implant is deployed is located outside the patient's body, which can facilitate visualization of the implant relative to the tissue and/or facilitate passage of a suture through the implant deployed in the tissue. In an exemplary embodiment, deployment outside of the patient's body occurs when the tissue in which the implant is positioned is synthetic tissue rather than natural tissue, e.g., tissue harvested or cultured from the patient.

Figure 9:
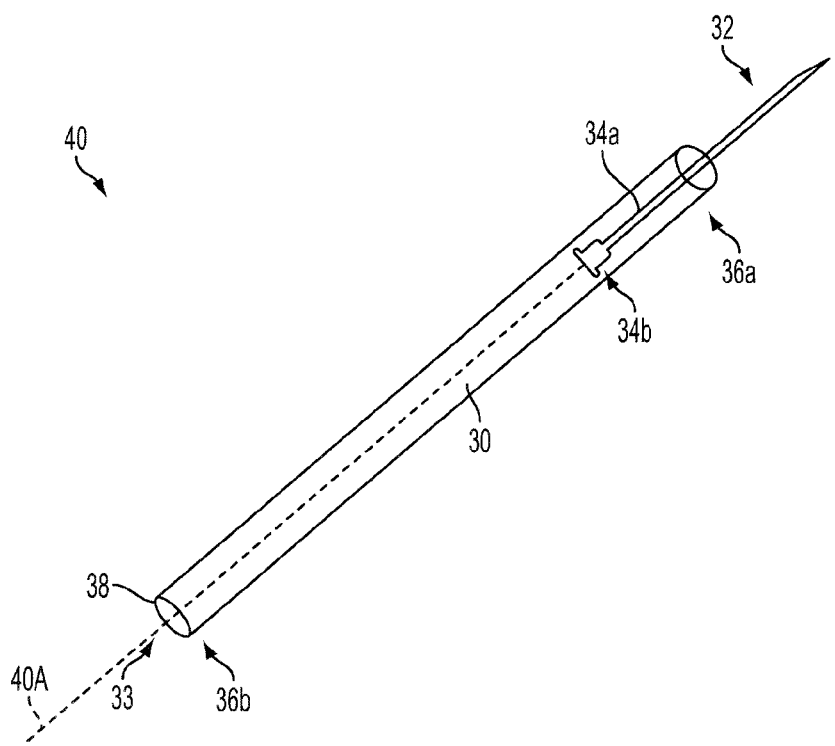
FIG. 9 is a perspective, partially transparent view of an embodiment of a delivery device having an embodiment of a pusher partially disposed therein.

FIG. 9 illustrates an exemplary embodiment of a delivery device 40 configured to deploy any of the implants discussed herein into tissue. The device 40 can include a cannulated elongate body 30 having a passageway 33 extending therethrough between proximal and distal ends 36a, 36b of the elongate body 30. The passageway 33 can be configured to receive an implant (not shown) received therein. The implant can be pre-loaded in the passageway, or it can be manually positioned therein prior to use of the implant. The elongate body 30 is shown as a standalone cannulated member having open proximal and distal ends 36a, 36b, but a cannulated elongate body of a delivery device can have a handle portion coupled to a proximal end thereof to facilitate handling of the delivery device and/or to facilitate advancing an implant therethrough.

The delivery device 40 can have a sharpened distal tip 38, e.g., a serrated edge, a sharp edge, a distally-extending knife, etc., configured to form a hole in tissue in which an implant is deployed. The sharpened distal tip 38 can reduce a number of tools needed to perform the procedure and/or save time. Alternatively or additionally, the delivery device 40 can be configured to have a cutting device, e.g., a knife, a needle, a cautery tool, a rotating burr, etc., inserted through the passageway 33 of the elongate body 30 to form the hole in tissue prior to the distal end 34b of the device 40 being advanced into the tissue. In some embodiments, however, a cutting device other than the delivery device and other than a cutting device advanced through the delivery device can be used to form the hole in the tissue, e.g., a standalone cutting device forming the hole prior to the distal end 34b of the delivery device 30 being positioned adjacent to the tissue.

The delivery device 40 can also include a pusher 32 configured to advance longitudinally through the passageway 33 along a longitudinal axis 40A of the device 40, e.g., coaxial with the axis 40A or substantially parallel thereto, to push an implant positioned in the passageway 33 therethrough and into a hole formed in the tissue. The pusher 32 can have a variety of sizes, shapes, and configurations. A distal end 34b of the pusher 32 can be configured to be inserted through the proximal end 36a of the elongate body 30 and into the passageway 33 of the delivery device 40 to engage a proximal end of the implant. The distal end 34b of the pusher 32 can have an enlarged diameter, e.g., be configured as a ball, a cone, a pyramid, a block, etc., compared to an elongate shaft 34a of the pusher 32. The enlarged diameter can facilitate contact of the pusher 32 with the implant while facilitating advancement of the shaft 34a through the passageway 33.

As mentioned above, in an exemplary embodiment, the implant can be pre-loaded into the passageway 33, but the implant can be loaded in the passageway 33 after the pusher 32 is inserted into the passageway 33, e.g., by being advanced through the distal end 36b of the elongate body 30. A proximal end (not shown) of the pusher 32 can include an actuator (not shown), and a user can engage the actuator to advance the pusher 32 distally through the passageway. The proximal end of the pusher 32 can also include a handle configured to facilitate handling of the pusher 32. The actuator can be coupled to the handle, e.g., be trigger-actuated at the handle, be a rotatable knob coupled to the handle, be a slidable lever coupled to the handle, etc.

The implants discussed herein can be used in attaching tissue to bone in a variety of surgical procedures, such as a procedure for attaching tissue to bone, e.g., anterior cruciate ligament (ACL) repair, rotator cuff repair, etc. In an exemplary embodiment, a procedure including implantation of the implant can be a minimally invasive procedure, but as will be appreciated by a person skilled in the art, the implants discussed herein also have application in open surgical instrumentation as well as application in robotic-assisted surgery.

FIGS. 10-14 illustrate an exemplary embodiment of securing soft tissue to bone including positioning an implant in a hole formed in tissue and passing a suture through the implant and the tissue. While FIGS. 10-14 show securing soft tissue to bone, the methods and devices disclosed herein can be used in a variety of medical procedures in which suture is passed through tissue, as mentioned above. Additionally, although FIGS. 10-14 are discussed with reference to the implant 100 of FIG. 1 and to the delivery device 40 and the pusher 32 of FIG. 9, any of the implants discussed herein can be advanced into tissue in this or other ways.

Figure 11:
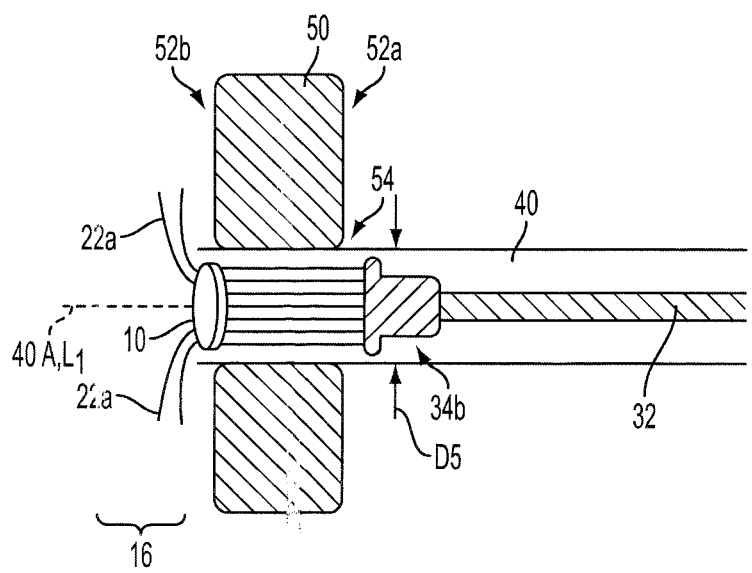
FIG. 11 is a side, partially transparent view of the implant of FIG. 10 being advanced out of the delivery device of FIG. 10 and into tissue.
Figure 12:
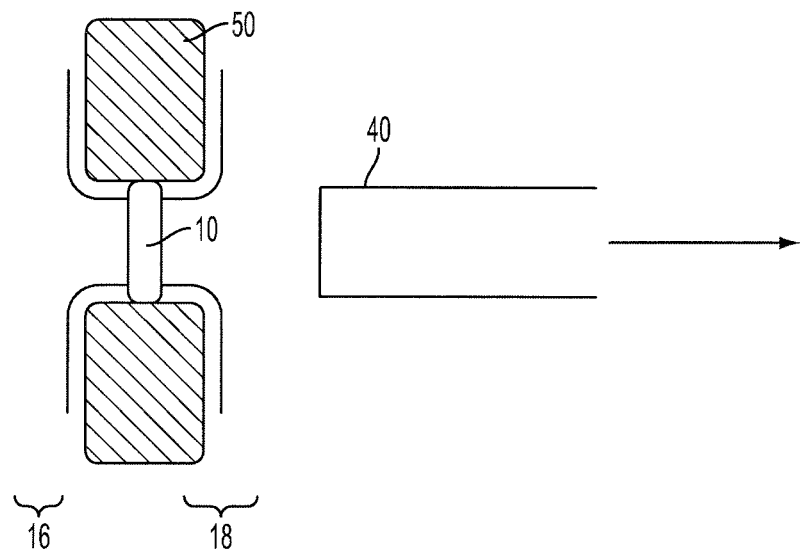
FIG. 12 is a side view of the implant of FIG. 11 positioned in the tissue and the delivery device being retracted away from the tissue.

The surgical procedure can include preparing the patient for surgery using standard techniques. In a minimally invasive procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. Although a cannula can be positioned in an incision and the delivery device 30 can be inserted therethrough, for clarity, the embodiments in FIGS. 10-12 show the delivery device 30 without an introducer device therearound.

Figure 10:
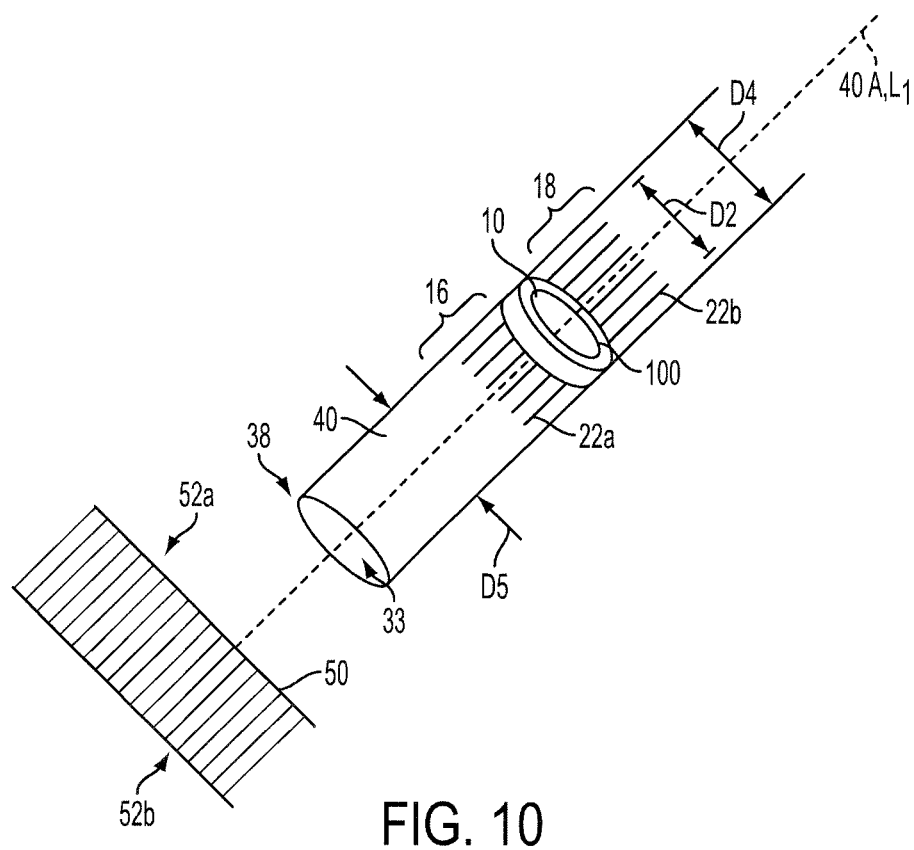
FIG. 10 a perspective, partially transparent view of the implant of FIG. 2 positioned in the delivery device of FIG. 9.

As shown in FIG. 10, the implant 100 can be positioned in the compressed configuration within the passageway 33 of the delivery device 40 for deployment in a tissue 50. When the implant 100 is positioned within the passageway 33 of the device 40, the first plurality of legs 22a can extend in a distal direction relative to the delivery device 40, and the second plurality of legs 22b can extend in a proximal direction relative to the delivery device 40. The implant 100 can be positioned within the passageway 33 in a variety of ways, such as by being advanced into the proximal end of the delivery device 40. The first radially expandable portion 16 of the implant 100 can be advanced first into the proximal end of the device 40 so that the first radially expandable portion 16 is the distal-most portion of the implant 100 within the passageway 33, followed by the intermediate portion 10 and the second radially expanding portion 18, as shown in FIG. 10. Alternatively, the implant 100 can be advanced into the distal end 36b of the delivery device 40. The second radially expanding portion 18 of the implant 100 can be advanced first into the distal end 36b of the device 40 so that the first radially expandable portion 16 is the distal-most portion of the implant 100 within the passageway 33, followed by the intermediate portion 10 and the second radially expanding portion 18.

As mentioned above, the maximum outer diameter D2 of the intermediate portion 10 can define a maximum diameter of the implant 10 in the compressed configuration. A maximum inner diameter D4 of the passageway 33 can therefore be larger than the maximum outer diameter D2 of the implant 100 so that the implant 100 can be positioned in the delivery device 40 and be slidably movable therein in a longitudinal direction, e.g., along the longitudinal axis 40A of the device 40 and along the longitudinal axis $L_1$ of the implant 100. When the implant 100 is positioned within the delivery device 40 in the compressed configuration, the longitudinal axis 40 of the device 40 can be coaxial with the longitudinal axis $L_1$ of the implant 100, as shown in FIG. 10, although the axes 40A, $L_1$ can be axially offset in other embodiments. As also mentioned above, when the implant 100 is in the compressed configuration, each of the legs 22a, 22b can be configured to be oriented substantially parallel to each other and to the longitudinal axis $L_1$ of the implant 100. Thus, when the implant 100 is positioned within the delivery device 40 in the compressed configuration, longitudinal axes of each of the first plurality of legs 22a, and longitudinal axes of each of the second plurality of legs 22b can be substantially parallel to each other and to the longitudinal axis of the delivery device 40A.

In the illustrated embodiment, the tissue 50 does not have a hole pre-formed therein to receive the implant 100. Instead, the distal tip 38 of the delivery device 40 can be configured to form a hole 54 in the tissue 50, shown in FIG. 11, by being advanced through a proximal surface 52a of the tissue 50 and advanced through the tissue 50 in a distal direction to advance the distal end 36b of the device 50 through a distal surface 52b of the tissue 50 to be located on a distal side of the tissue 50. The hole 54 can therefore have a diameter substantially equal to an outer diameter D5 of the delivery device 40. The hole 54 can therefore have a diameter sized to have the intermediate portion 10 of implant 100 positioned therein in a relatively snug fit. The hole 54 can be formed to have such a diameter even if the distal end 36b of the device 40 does not cut through the tissue 50, but using the distal end 36b of the device 40 in this way can be easier and faster than otherwise measuring the hole 54 to be a correct size. If a cutting device is used to form the tissue hole 54 rather than the device's distal end 36b alone, the cutting device can be retracted in a proximal direction out of the tissue 50 after the hole 54 is formed to help prevent the cutting device from interfering with deployment of the implant 100 within the hole 54.

The distal end 36b of the delivery device 40 can be advanced in a distal direction through the hole 54 to be positioned in alignment with the distal surface 52b of the tissue, or in an exemplary embodiment, distal to the distal surface 52b of the tissue 50. This position can be visually detected, e.g., using a visualization device such as a scope, and/or can be detected by feel, e.g., a user of the delivery device 40 detecting a reduction in force or tension when the device's distal end 36b passes through the tissue 50. The first radially expanding portion 16 of the implant 100 can then be advanced out of the delivery device 40, e.g., by pushing the pusher 32 through the device's passageway 33 in a distal direction, relative to the device 40 and to the implant 100, with the distal end 34b of the pusher 32 abutting the second radially expanding portion 18 of the implant 100, to position the first radially expanding portion 16 on the distal side of the tissue 50. When the first radially expanding portion 16 exits the delivery device 40 through the distal end 36b thereof, a force constraining the first radially expanding portion 16, e.g., a force applied by an internal surface of the device 40, is removed, thereby allowing the first radially expanding portion 16 to automatically radially expand in a direction away from the longitudinal axis $L_1$ of the implant 100, as shown in FIG. 11. The implant 100 can thus be in a partially deployed configuration in which one of the radially expanding portions 16, 18 is expanded, e.g., the first radially expanding portion 16 being radially expanded outside the delivery device 40, and the other one of the radially expanding portions 16, 18 is compressed, e.g., the second radially expanding portion 18 being compressed within the delivery device 40.

After the first radially expanding portion 16 of the implant 100 is advanced out of the delivery device 40, the second radially expanding portion 18 of the implant 100 can be advanced out of the delivery device 40, thereby moving the implant 100 to the expanded configuration. In an exemplary embodiment, the second radially expanding portion 18 can be advanced out of the delivery device 40 by advancing the delivery device 40 in a proximal direction relative to the implant 100. If the pusher 32 has not already been removed from the passageway 33 of the device 40, e.g., by pulling the pusher 32 proximally, the pusher 32 can also be advanced in a proximal direction relative to the implant 100 to allow deployment of the second radially expanding portion 18. In other words, the pusher 32 can be moved in opposite directions to deploy the first and second radially expanding portions 16, 18, in a distal direction to deploy the first radially expanding portion 16 and in a proximal direction to deploy the second radially expanding portion 18. Alternatively, delivery device 40 can be advanced in a proximal direction simultaneously with the pusher 32 being advanced in a distal direction to push against the second radially expanding portion 18, thereby allowing the pusher 32 and the device 40 to cooperate in removing the second radially expandable portion 18 from the device 40.

The first radially expandable portion 16 being positioned on the distal side of the tissue 50 when the second radially expanding portion 18 exits the delivery device 40 can provide adequate tension, e.g., by the first plurality of legs 22a abutting against the distal tissue surface 52b, to allow the delivery device 40 and/or the pusher 32 to be moved relative to the implant 100 to deploy the second radially expanding portion 18 without advancing the entire implant 100 proximally through the hole 54. When the second radially expanding portion 18 exits the delivery device 40 through the distal end 36b thereof, a force constraining the second radially expanding portion 18, e.g., a force applied by the internal surface of the device 40, can be removed, thereby allowing the second radially expanding portion 18 to automatically radially expand in a direction away from the longitudinal axis $L_1$ of the implant 100, as shown in FIG. 12.

Moving the delivery device 40 and/or the pusher 32 to deploy the second radially expanding portion 18 can also cause the intermediate portion 10 of the implant 100 to be positioned within the hole 54. In an exemplary embodiment, when the implant 100 is positioned in the hole 54, the channel 12 of the intermediate portion 10 can be positioned substantially parallel to a longitudinal axis of the hole 54, thereby allowing a suture to be more easily passed therethrough and exit therefrom at a more predictable angle relative to the tissue.

When the implant 100 is in the expanded configuration and deployed in the tissue 50, as shown in FIG. 12, the first plurality of legs 22a can be configured to expand or bend along the distal surface 52b of the tissue 50 such that substantial portions of each of the first plurality of legs 22a contact the distal tissue surface 52b. Similarly, the second plurality of legs 22b can be configured to expand or bend along the proximal surface 52a of the tissue 50 such that substantial portions of each of the second plurality of legs 22b contact the proximal tissue surface 52a. While the legs 22a, 22b in the illustrated embodiment have a substantially straight configuration along the tissue surfaces 52a, 52b, as shown in FIG. 12, the legs can have a curved configuration and/or terminal ends of any or all of the legs can be configured to curve away from the tissue 50.

As shown in FIG. 12, when the implant 100 is deployed in the tissue 50, an entirety of the intermediate portion 10 can be positioned within the hole 54 such that the intermediate portion 10 does not span a depth of the hole 54, and the legs 22a, 22b can be partially positioned within the hole. First portions of each of the first and second plurality of legs 22a, 22b can be positioned within the hole 54, and second portions of each of the first and second plurality of legs 22a, 22b can be positioned outside the hole 54, e.g., along the tissue surfaces 52a, 52b. Having portions of the legs 22a, 22b positioned within the hole 54 can help securely retain the implant 100 therein. In another embodiment, the legs can be positioned entirely outside the tissue hole and/or the intermediate portion can be only partially positioned within the hole such that the intermediate portion does span the depth of the hole.

Figure 13:
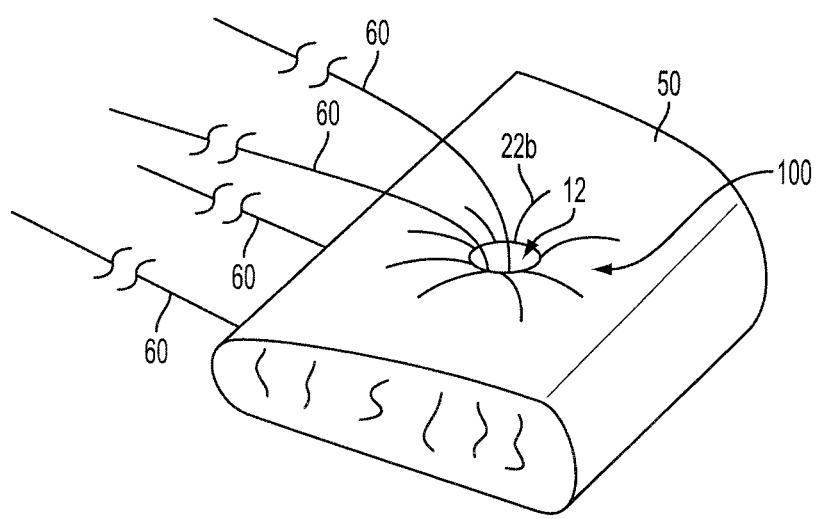
FIG. 13 is a perspective view a plurality of sutures extending through the implant and the tissue of FIG. 12.

With the implant 100 positioned within the tissue hole 54, at least one suture 60 can be advanced through the channel 12 of the implant 100, as shown in FIG. 13. Although two sutures 60 with four trailing ends are shown in FIG. 13, any number of sutures can be advanced through the implant 100, and each of the sutures can be looped through the implant's channel 12 any number of times. In an exemplary embodiment, the at least one suture 60 can be passed through the intermediate portion 10 of the implant 100 after the implant 100 has been positioned in the tissue hole 54, which can help prevent the at least one suture 60 from tangling with the implant 100 and/or the pusher 32 during advancement through the delivery device 40 and/or help prevent the at least one suture 60 from tangling with the radially expanding portions 16, 18 of the implant 100 as they radially expand. In another embodiment, one or more sutures can be inserted through the implant 100 prior to the implant 100 being positioned within the tissue 50, e.g., pre-loaded into the delivery device 40.

The at least one suture 60 coupled to the implant 100, and hence the tissue 50, can be used to secure the tissue 50 at a desired site in the body. In an exemplary embodiment, the tissue 50 can be attached to a bone using a suture anchor.

Figure 14:
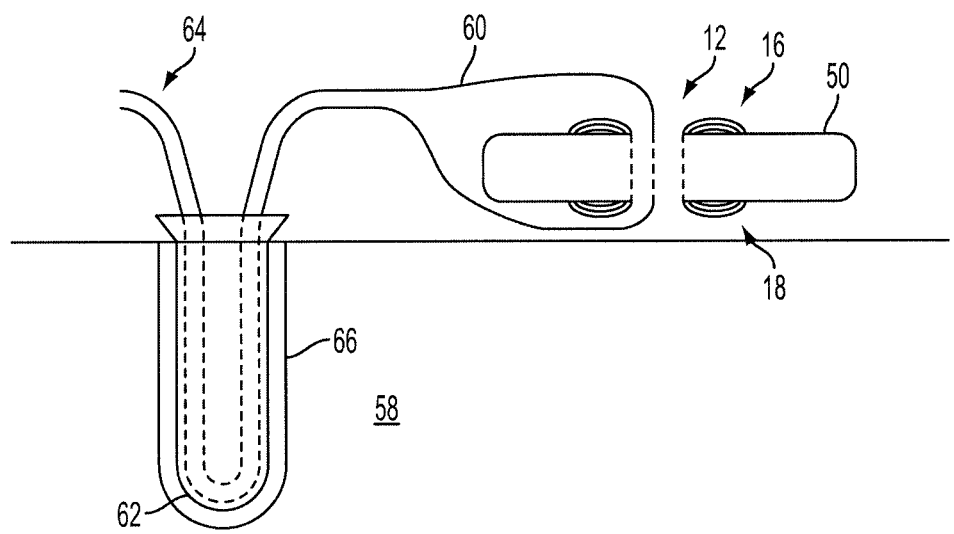
FIG. 14 is a side, partially transparent view of a bone anchor having the implant, the tissue, and the sutures of FIG. 13 coupled thereto.

As shown in FIG. 14, a bore, bone hole, or bone tunnel 66, generally referred to herein as a "bone tunnel," can be formed in bone 58 of the patient. The bone tunnel 66 can be pre-formed, such as by using a drill, an awl, a punch instrument, etc., as will be appreciated by a person skilled in the art. Alternatively, the bone tunnel 66 can be formed simultaneously with advancement of a suture anchor 62 into the bone 58 and simultaneously with threadable engagement of the anchor 62 therewith, such as by using a self-awling or self-tapping driver and/or self-awling or self-tapping anchor. The bone tunnel 66 can extend fully through cortical bone to allow the suture anchor 62 to be fully engaged through the thickness of the cortical bone. The bone tunnel 66 can also extend into cancellous bone located underneath the cortical bone. The bone tunnel 66 can be formed in the bone 58 before or after the implant 100 is deployed in the tissue 50. Similarly, the suture anchor 62 can be deployed in the bone tunnel 66 before or after the implant 100 is deployed in the tissue 50, and before or after the at least one suture 60 is coupled to the suture anchor 62. For clarity, only one of the two sutures 60 of FIG. 13 is shown in FIG. 14. As will be appreciated by a person skilled in the art, the suture anchor 62 can have a variety of configurations. Non-limiting examples of suture anchors and deploying suture anchors into bone are described in further detail in U.S. application Ser. No. 11/555,545 entitled "Cannulated Suture Anchor" filed Feb. 1, 2006, now U.S. Pat. No. 8,114,128, U.S. application Ser. No. 11/855,670 entitled "Dual Thread Cannulated Suture Anchor" filed Sep. 14, 2007, and U.S. application Ser. No. 10/615,625 entitled "Bioabsorbable Suture Anchor System For Use In Small Joints" filed Jun. 27, 2003, now U.S. Pat. No. 8,133,257, which are hereby incorporated by reference in their entireties.

With the at least one suture 60 coupled to the suture anchor 66 disposed in the bone tunnel 62, and with the at least one suture 60 coupled to the implant 100 deployed in the tissue 50, the suture 64 can be tensioned in any way, as will be appreciated by a person skilled in the art, such as by pulling on ends 64 thereof. The suture tensioning can cause the tissue 50 to better contact bone 58 and/or move toward a suture anchor 62 secured in bone 58. Because the suture 60 can extend through the implant 100 in the tissue 50, the implant 100 can reduce the risk of the suture 60 breaking through the tissue 50 during and/or following the tensioning. This in turn can help ensure that the tissue maintains contact with the bone during and after the surgical procedure, facilitating healing.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the legs, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
    advancing an implant in a first configuration through a cannula, the implant having an intermediate portion with a first radially expanding portion extending distally therefrom and a second radially expanding portion extending proximally therefrom;
    advancing the implant distally out of the cannula to position the implant within an opening formed in soft tissue, the implant moving from the first configuration to a second radially expanded configuration such that the first radially expanding portion of the implant is positioned on a distal side of the opening, the second radially expanding portion of the implant is positioned on a proximal side of the opening, and the intermediate portion is positioned within the opening;
    advancing a suture through the intermediate portion positioned in the soft tissue;
    advancing an anchor into a bone; and
    securing the tissue in position relative to the bone, the suture advanced through the intermediate portion being coupled to the bone to facilitate the securing.

2. The method of claim 1, wherein the implant is formed from a shape memory material such that the implant is biased to the second configuration.

3. The method of claim 1, wherein advancing the implant distally out of the cannula comprises advancing the first radially expandable portion out of the cannula before the second radially expandable portion is advanced out of the cannula.

4. The method of claim 1, wherein a maximum outer diameter of the implant in the first configuration is less than a maximum inner diameter of an inner passageway of the cannula in which the implant is disposed, and a maximum outer diameter of the implant in the second configuration is greater than the maximum inner diameter of the inner passageway.

5. The method of claim 1, wherein the first radially expandable portion comprises a first plurality of legs extending distally from the intermediate portion, and the second radially expandable portion comprises a second plurality of legs extending proximally from the intermediate portion.

6. The method of claim 5, wherein, when the implant is in the first configuration, the first plurality of legs and the second plurality of legs are each substantially straight, and when the implant is in the second configuration, the first plurality of legs and the second plurality of legs are each bent.

7. The method of claim 5, wherein when the implant is in the first configuration, longitudinal axes of each of the first plurality of legs extend substantially parallel to longitudinal axes of each of the second plurality of legs and to a longitudinal axis of the cannula, and when the implant is in the second configuration, the longitudinal axes of the first plurality of legs and the longitudinal axes of each of the second plurality of legs extend transverse to the longitudinal axis of the cannula.

8. The method of claim 5, wherein advancing the implant distally out of the cannula comprises advancing the first plurality of legs out of the cannula before the second plurality of legs are advanced out of the cannula.

9. The method of claim 8, wherein, when the first plurality of legs out of the cannula are advanced out of the cannula before the second plurality of legs are advanced out of the cannula, the implant is in a third configuration in which the longitudinal axes of the first plurality of legs extend transverse to the longitudinal axis of the cannula and the longitudinal axes of the second plurality of legs are substantially parallel to the longitudinal axis of the cannula.

10. The method of claim 1, wherein the first radially expandable portion includes a first fabric extending distally from the intermediate portion, and the second radially expandable portion includes a second fabric extending proximally from the intermediate portion.

11. The method of claim 10, wherein the first fabric and the second fabric are formed from one continuous piece of fabric.

12. The method of claim 1, further comprising, prior to advancing the implant out of the cannula, forming the opening in the soft tissue.

13. The method of claim 1, further comprising, after advancing the suture, tensioning the suture relative to a bone.

14. A surgical method, comprising:
    advancing an introducer device at least partially through an opening formed in tissue, the introducer device having an implant disposed in an inner passageway thereof;
    moving a first radially expanding portion of the implant out of the inner passageway, thereby causing the first radially expanding portion to be positioned on a distal side of the opening, the first radially expanding portion expanding into contact with a distal surface of the tissue;
    moving a second radially expanding portion of the implant out of the inner passageway to position the second radially expanding portion on a proximal side of the opening, the second radially expanding portion expanding into contact with a proximal surface of the tissue, and a hollow intermediate portion of the implant extending between the first radially expanding portion and the second radially expanding portion being positioned within the opening, the hollow intermediate portion having a continuous inner wall;
    advancing a suture through the hollow intermediate portion positioned within the opening;
    advancing an anchor into a bone; and securing the tissue in position relative to the bone, the suture advanced through the intermediate portion being coupled to the bone anchor to facilitate the securing.

15. The method of claim 14, wherein moving the first radially expanding portion comprises moving the implant distally relative to the introducer device, and moving the second radially expanding portion comprises moving the introducer device proximally relative to the implant.

16. The method of claim 14, wherein moving the first radially expanding portion of the implant out of the inner passageway causes the first radially expanding portion to automatically expand radially away from a central longitudinal axis of the implant, and moving the second radially expanding portion of the implant out of the inner passageway causes the second radially expanding portion to automatically expand radially away from the central longitudinal axis of the implant.

17. The method of claim 14, further comprising forming the opening in the tissue by performing at least one of advancing the introducer device through the tissue and cutting through the tissue.

18. The method of claim 14, wherein the first radially expandable portion comprises a first plurality of legs extending distally from the hollow intermediate portion, and the second radially expandable portion comprises a second plurality of legs extending proximally from the hollow intermediate portion.

19. The method of claim 14, wherein advancing the suture through the hollow intermediate portion positioned within the opening comprises introducing a free end of the suture into the hollow intermediate portion positioned within the opening.

\* \* \* \* \*